US00PP28464P2

(12) United States Plant Patent
Egger

(10) Patent No.: US PP28,464 P2
(45) Date of Patent: Sep. 26, 2017

(54) ***KNIPHOFIA* PLANT NAMED 'POCO SUNSET'**

(50) Latin Name: ***Kniphofia* spp.**
Varietal Denomination: Poco Sunset

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 15/330,219

(22) Filed: Aug. 25, 2016

(51) Int. Cl.
*A01H 5/02* (2006.01)

(52) U.S. Cl.
USPC ..... Plt./443

(58) Field of Classification Search
USPC ..... Plt./443
CPC ..... A01H 5/02
See application file for complete search history.

(56) References Cited

PUBLICATIONS http://www.nurserymag.com/product/terra-nova-poco-red/; Apr. 11, 2016; 1 page.*

* cited by examiner

*Primary Examiner* — Kent L Bell
(74) *Attorney, Agent, or Firm* — Klarquist Sparkman, LLP

(57) ABSTRACT

A new and distinct *Kniphofia* plant characterized by its habit of forming multiple crowns fast and each crown produces inflorescences in the first season, inflorescences of bicolor red orange and coral flowers on short stems, a very long bloom time with repeat blooming from July through October in Canby, Oreg., a short habit, narrow, grassy, short leaves, and excellent vigor.

1 Drawing Sheet

Botanical denomination: *Kniphofia* spp. (hybrid, species unknown).

Cultivar designation: 'Poco Sunset'.

BACKGROUND OF THE INVENTION

The present invention relates to a new and distinct *Kniphofia*, and given the cultivar name is 'Poco Sunset'. *Kniphofia* is in the family Xanthorrhoeaceae. 'Poco Sunset' is a hybrid resulting from a planned breeding program to produce short, compact, reblooming *Kniphofia*. The cross was made using the following proprietary, unreleased plants: *Kniphofia* 'K58-3', as the seed parent and 'K64-1', as the pollen parent. The new cultivar, 'Poco Sunset' was selected for best habit, flower color, reblooming, and crown count from many seedlings of the cross in Canby, Oreg.

Compared to *Kniphofia* 'K58-3', the seed parent, the new cultivar is more free-flowering and has bicolor red orange and coral flowers rather than red. Compared to *Kniphofia* 'K64-1', the pollen parent, the new cultivar is earlier blooming and more free-flowering. Compared to *Kniphofia* 'Ember Glow', U.S. Plant Pat. No. 23,000, the new cultivar is shorter with shorter leaves in a denser habit. The flowers of the new cultivar are bicolor red orange and coral rather than orange and yellow.

Compared to *Kniphofia* 'Fire Glow', U.S. Plant Pat. No. 22,894, the new cultivar has shorter leaves and inflorescences and has flowers that are red orange and coral rather than red and yellow.

SUMMARY OF THE INVENTION

The new cultivar is unique and characterized by:

1. its habit of forming multiple crowns fast and each crown produces inflorescences in the first season, 2. inflorescences of bicolor red orange and coral flowers on short stems,
3. a very long bloom time with repeat blooming from July through October in Canby, Oreg.,
4. a short habit,
5. narrow, short, grassy leaves, and
6. excellent vigor.

This new cultivar has been reproduced only by asexual propagation (division, tissue culture). Each of the progeny exhibits identical characteristics to the new cultivar. Asexual propagation by leaf cuttings, tissue culture, and division using standard techniques as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a 9 month old plant in the trial field in July in Canby, Oreg.

FIG. 2 shows a 1 and a half year-old *Kniphofia* 'Poco Sunset' in the ground in the trial field in August in Canby, Oreg.

DETAILED PLANT DESCRIPTION

The following is a detailed description of the new *Kniphofia* cultivar based on observations of 7 month-old specimens growing outside in full sun in the trial field in late September in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on *The Royal Horticultural Society Colour Chart,* $5^{th}$ edition, 2007.

Plant:

*Type*.—Rhizomatous herbaceous perennial.

*Hardiness*.—USDA Zones 7 to 9.

*Size*.—Grows to 38 cm wide and 51 cm to 58 cm tall from the top of the soil to the top of the inflorescences and 30 cm to 45 cm from the soil to the top of the leaves.

*Crown #*.—About 20.

*# Leaves/crown*.—About 11.

*# Inflorescences/crown*.—1 to 2.

*Form*.—Clumping.

Leaf:

*Type*.—Simple.

*Shape*.—Strap-like, keeled.

*Arrangement*.—Basal rosette.

*Blade size*.—30 cm to 50 cm long and 7 mm to 9 mm wide (near the base).

*Margins*.—Entire.

*Apex*.—Acuminate.

*Base*.—Clasping.

*Surface texture*.—Glabrous on both sides.

*Venation*.—Parallel, Green 137A on both sides.

*Color*.—Top and bottom side Green 137A.

Inflorescence:

*Type*.—Spike-like scapose raceme.

*Number of flowers per raceme*.—About 80.

*Inflorescence*.—21.5 cm long and 6.5 cm wide.

*Peduncle description*.—Grows to 25 cm long and 8 mm wide, glabrous, Yellow Green 146A.

*Pedicel description*.—Grows to 2 mm long and less than 1 mm wide, glabrous, Greyed Orange 174A.

*Bloom time*.—July through October in Canby, Oreg.

*Lastingness*.—An inflorescence lasts for 2 to 4 weeks and an individual flower lasts about 5 days depending on the temperature.

Flower bud:

*Size*.—28 mm long and 6 mm wide.

*Shape*.—Cylindrical.

*Surface texture*.—Glabrous.

*Color*.—Red Orange 35A.

Flower:

*Type*.—Actinomorphic.

*Shape*.—Cylindrical and tubular.

*Size*.—Grows to 28 mm deep and 12 mm wide.

*Texture*.—Waxy.

*Surface texture*.—Glabrous on both sides.

*Corolla description*.—28 mm long and 12 mm wide, 6-lobed fused tepals, tube 25 mm long and 7 mm wide, lobes reflex, each 3 mm wide and 4 mm long, ovate, entire, acute; color inside Orange 29B and outside Yellow Orange 20B on the lower flowers to Orange Red 32C.

*Pistil description*.—One, 25 mm long, ovary 2.5 mm long 1.5 mm wide, Yellow Green 146C, style 22.5 mm long, Greyed Orange N167D, stigma Greyed Orange 172A.

*Stamen*.—6, 28 mm long, filaments 27 mm long, Yellow Green 150D, anthers 1 mm long and Yellow Orange 22A, pollen slight, Yellow 8B.

*Fragrance*.—None.

Fruit and seed: No mature fruit formed, no seed produced.

Pest and diseases: Pests and diseases are infrequent on *Kniphofia* spp. No problems have been observed on this plant grown under commercial conditions in Canby, Oreg.

I claim:

1. A new and distinct *Kniphofia* plant as herein shown and described.

* * * * *

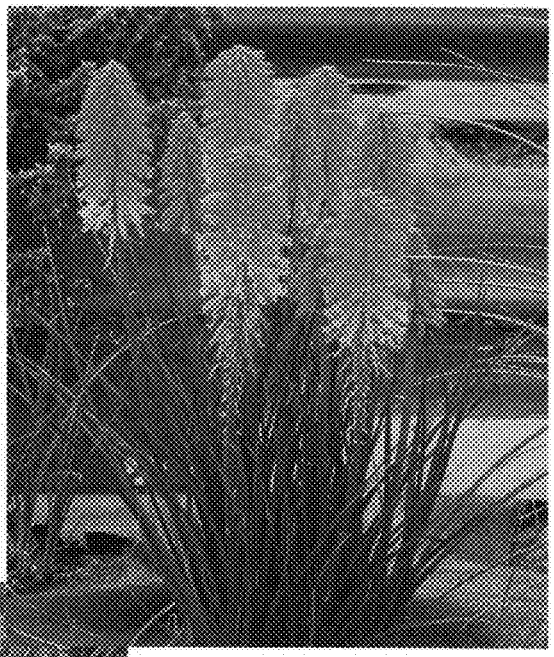
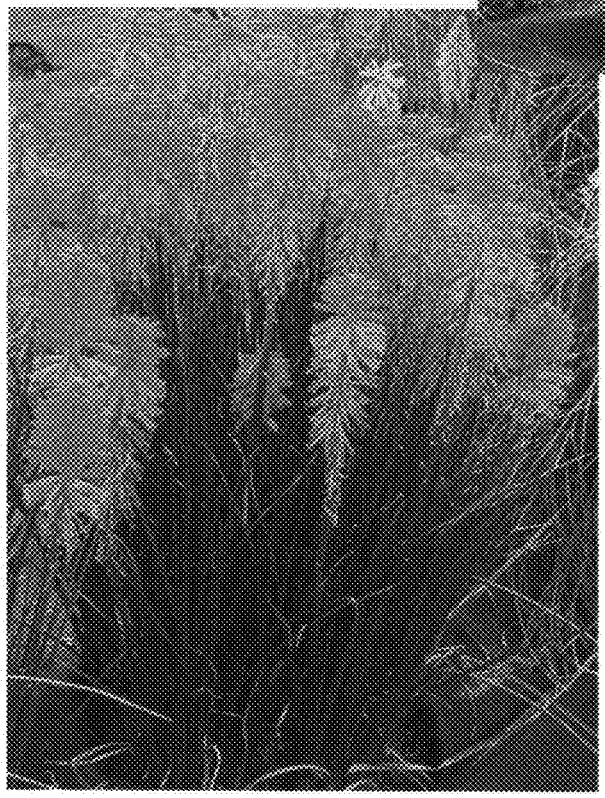
FIG 1 above.
FIG. 2 on left